United States Patent [19]

Ohashi et al.

[11] Patent Number: 4,460,780

[45] Date of Patent: Jul. 17, 1984

[54] PROCESS FOR PREPARATION OF OPTICALLY ACTIVE THIOL COMPOUNDS

[75] Inventors: Takehisa Ohashi, Kobe; Masami Shimazaki, Takasago; Kenji Nomura, Akashi; Yasushi Nose, Takasago; Kiyoshi Watanabe, Akashi, all of Japan

[73] Assignee: Kanegafuchi Chemical Industry Company, Ltd., Osaka, Japan

[21] Appl. No.: 457,377

[22] Filed: Jan. 12, 1983

[30] Foreign Application Priority Data

Jan. 20, 1982 [JP] Japan .................................. 57-7803

[51] Int. Cl.$^3$ .................. C07D 207/16; C07D 277/06
[52] U.S. Cl. ..................................... 548/201; 548/533
[58] Field of Search ................................ 548/533, 201

[56] References Cited

U.S. PATENT DOCUMENTS 4,332,725 6/1982 Fisher ................................... 548/533

FOREIGN PATENT DOCUMENTS 2066252 7/1981 United Kingdom ................ 548/201

Primary Examiner—Robert Gerstl
Attorney, Agent, or Firm—Armstrong, Nikaido, Marmelstein & Kubovcik

[57] ABSTRACT

An improved process for preparation of an optically active N-(3-mercapto-2-D-methylpropanoyl)-L-amino acid represented by formula (I):

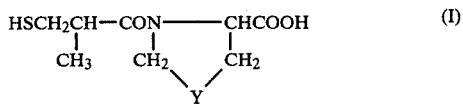

from an N-(3-chloro-2-D-methylpropanoyl)-L-amino acid represented by formula (II):

$$Cl-CH_2CH-CON\underset{CH_2\diagdown Y\diagup CH_2}{\overset{|}{\underset{CH_3}{}}}CHCOOQ \quad (II)$$

(Y in (I) and (II): $CH_2$ or sulfur; Q in (II): hydrogen, Na, K or $NH_4$), which is characterized by reacting the compound (II) with an alkali trithiocarbonate, of which the molar ratio to the compound (II) is not less than 1.5, in an aqueous medium at a temperature of from about 60° C. to about 90° C., and hydrolyzing the resulting product with an acid.

It is preferable to use sodium trithiocarbonate as the alkali trithiocarbonate, mineral acid as the acid, or water or aqueous alcohol as an aqueous medium.

5 Claims, No Drawings

PROCESS FOR PREPARATION OF OPTICALLY ACTIVE THIOL COMPOUNDS

BRIEF SUMMARY OF THE INVENTION

The present invention relates to a process for preparation of an optically active N-(3-mercapto-2-D-methylpropanoyl)-L-amino acid represented by formula (I):

$$HSCH_2-\underset{H}{\underset{|}{\overset{CH_3}{\overset{|}{C}}}}-CON\underset{\underset{Y}{CH_2\diagdown\diagup CH_2}}{-CHCOOH} \quad (I)$$

wherein Y is $CH_2$ or sulfur.

The product of the present invention inhibits the enzymatic conversion of angiotensin I into angiotensin II and therefore is useful in reducing or relieving angiotensin-related hypertension. [M. A. Ondetti et al., Biochemistry, 16, 5484 (1977): The Medical Journal of Australia, Vol. 2, P.1 "Symposium on Converting Enzyme Inhibition in Hypertension" (1979)]. The compound specified above with D configuration in the mercaptoalkanoyl side chain is about 100 times more potently inhibitory against the enzyme than the corresponding L-enantiomer.

The preparation of D-enantiomer of N-mercaptoalkanoylamino acids, for example, N-(3-mepcapto-2-D-methylpropanoyl)-L-proline, has thus far involved a troublesome optical resolution [M. A. Ondetti et al., U.S. Pat. Nos. 4,046,889 (1977), 4,105,776 (1978), 4,154,840 (1979)].

Moreover, the known processes for their production include the reaction of an N-ω-haloalkanoylamino acid with an anion of a thioacid such as thiolacetic acid or thiobenzoic acid in order to produce an N-acylthioalkanoylamino acid; therefore, the acyl group as a protecting group for the thiol group must finally be removed to obtain the desired N-mercaptoalkanoylamino acid.

As mentioned above, known processes for producing optically active N-mercaptoalkanoyl ammino acids include complicated optical resolution, usage of reagents for protection of the thiol group.

An improved process has been developed by the present inventors (U.S. Pat. application Ser. No. 214,780/1980).

In the above patent application, the simplified process for preparation of an optically active N-mercaptoalkanoyl-amino acid (I) by reacting an optically active N-β-haloalkanoyl-amino acid (II) with NaSH or NH4SH.

$$ClCH_2-\underset{H}{\underset{|}{\overset{CH_3}{\overset{|}{C}}}}-CON\underset{\underset{Y}{CH_2\diagdown\diagup CH_2}}{-CHCOOQ} \xrightarrow{NaSH\ or\ NH_4SH}$$

(II)

$$HSCH_2-\underset{H}{\underset{|}{\overset{CH_3}{\overset{|}{C}}}}-CON\underset{\underset{Y}{CH_2\diagdown\diagup CH_2}}{-CHCOOH} \quad (I)$$

(Y=$CH_2$ or S, Q=Na, K or $NH_4$)

However, in the process described above, the undesired byproduct, monosulfide compound (III), was observed and therefore in order to obtain the compound (I) possessing high purity in a good yield the usage of the excess amount of NaSH or NH4SH to the compound (II) and the lowering of the concentration of the compound (II) in the reaction system were needed.

$$S(CH_2-\underset{H}{\underset{|}{\overset{CH_3}{\overset{|}{C}}}}-CON\underset{\underset{Y}{CH_2\diagdown\diagup CH_2}}{-CHCOOH})_2 \quad (III)$$

The object of the present invention is therefore to provide more improved process for preparing an optically active N-mercaptoalkanoylamino acid. The present inventors carried out researches in order to establish an improved process for preparing an optically active N-mercaptoalkanoylamino acid from an optically active N-β-haloalkanoylamino acid and have now completed the present invention.

The present invention is a process for preparation of an optically active N-(3-mercapto-2-D-methylpropanoyl)-L-amino acid represented by formula (I):

$$HSCH_2-\underset{H}{\underset{|}{\overset{CH_3}{\overset{|}{C}}}}-CON\underset{\underset{Y}{CH_2\diagdown\diagup CH_2}}{-CHCOOH} \quad (I)$$

wherein Y is $CH_2$ or sulfur, which comprises
(1) reacting an N-(3-chloro-2-D-methylpropanoyl)-L-amino acid represented by formula (II)

$$ClCH_2-\underset{H}{\underset{|}{\overset{CH_3}{\overset{|}{C}}}}-CON\underset{\underset{Y}{CH_2\diagdown\diagup CH_2}}{-CHCOOQ} \quad (II)$$

wherein Y is the same as defined above, and Q is hydrogen, Na, K, or $NH_4$ with an alkali trithiocarbonate and
(2) hydrolyzing the resulting product with an acid.

$$(II)\ +\ MS-\underset{\underset{S}{\|}}{C}-SM\ \longrightarrow$$

$$(MS-\underset{\underset{S}{\|}}{C}-SCH_2-\underset{H}{\underset{|}{\overset{CH_3}{\overset{|}{C}}}}-CON\underset{\underset{Y}{CH_2\diagdown\diagup CH_2}}{-CHCOOH(M))} \xrightarrow{H^+} (I)$$

(M=Na, K or NH4)

According to the present invention, an optically active N-mercaptoalkanoylamino acid (I) can be obtained starting from an optically active N-(3-chloro-2-D-methylpropanoyl)-L-amino acid (II) in a simple process which involves neither the step of optical resolution nor the step of protection of the thiol group as explained hereinbefore.

Further, a high purity of N-mercaptoalkanoylamino acid (I) can be easily obtained in a high yield by the retardation of the formation of undesired by-product, monosulfide compound (III).

The starting material of the present invention, the compound (II) can be produced industrially according to inventions by some of the present inventors in which the compound (II) is produced by the reaction of optically active 3-chloro-2-D-methylpropanoyl chloride (V) with L-proline or L-thiazolidine-4-carboxylic acid. (U.S. Pat. application Ser. No. 214,780/1980)

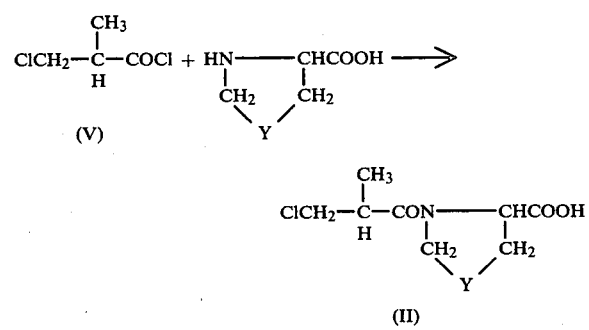

(Y=CH2 or S)

Optically active 3-chloro-2-D-methylpropanoyl chloride can be easily prepared from 3-hydroxy-2-D-methylpropanoic acid (VI) which is readily produced by subjecting isobutyric acid or methacrylic acid to the stereospecific action of specific microorganisms. (U.S. Pat. No. 4,310,635)

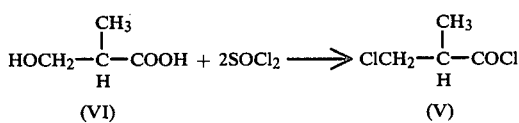

Therefore, the present invention is very advantageous in that the starting material, N-(3-chloro-2-D-methylpropanoyl)-L-amino acid, is readily available industrially and a high purity of N-(3-mercapto-2-D-methylpropanoyl)-L-amino acid can be easily obtained in a good yield.

Concerning to the present invention, a process for the preparation of N-(3-mercapto-2-D-methylpropanoyl)-L-proline by the reaction of N-(3-bromo-2-D-methylpropanoyl)-L-proline with alkali trithiocarbonate was reported by J. Fischer et al., (UK Patent Application non-examined publication No. 2,066,252 A (1981))

In the published patent application, a process for the preparation of 3-mercapto-2-D-methylpropanoyl-L-proline by the reaction of N-(3-halo-2-D-methylpropanoyl)-L-proline with alkali trithiocarbonate followed by acid hydrolysis is claimed, but in the specification, no examples as to reactions using N-(3-chloro-2-D-methylpropanoyl)-L-proline is described.

From the aspect of industrial availability N-(3-chloro-2-D-methylpropanoyl)-L-proline can be produced more easily than N-(3-bromo-2-D-methylpropanoyl)-L-proline.

On the other hand, N-(3-bromo-2-D-methylpropanoyl)-L-proline should be prepared by the following multistep reaction using corrosive hydrogen bromide, and therefore, N-(3-bromo-2-D-methylpropanoyl)-L-proline is inadequate as a starting material.

In the above published patent application it was described that N-(3-bromo-2-D-methylpropanoyl)-L-proline was reacted with almost equimolar alkali trithiocarbonate at mild temperature to form N-(3-mercapto-2-D-methylpropanoyl)-L-proline.

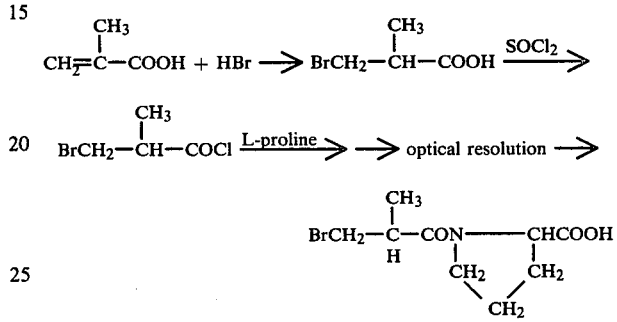

However, the present inventors found, as shown in comparative experiment, that the reaction using N-(3-chloro-2-D-methylpropanoyl)-L-proline did not proceed in a sufficient yield under the same conditions as those for 3-bromo analogue disclosed in the abovementioned GB 2,066,252 A.

The present inventors have investigated precisely the reaction of N-(3-chloro-2-D-methylpropanoyl)-L-proline (II) with alkali trithiocarbonate and compared the reactivity of the compound (II) with N-(3-bromo-2-D-methylpropanoyl)-L-proline.

Surprisingly in the reaction using the compound (II) the extent of the formation of the by-product, monosulfide compound (III), varied largely with the reaction condition.

On the other hand, in the reaction using N-(3-bromo-2-D-methylpropanoyl)-L-proline as a starting material the formation of the monosulfide compound was not so largely affected by the reaction condition.

The molar ratio of alkali trithiocarbonate to N-(3-chloro-2-D-methylpropanoyl)-L-proline was the important factor to affect the extent of the formation of the monosulfide compound. The reaction temperature was estimated to affect the reaction velocity. The comparative data concerning to the reactions using N-(3-chloro-2-D-methylpropanoyl)-L-proline and N-(3-bromo-2-D-methylpropanoyl)-L-proline are described in example 5.

As shown from data described in example 5, not less than 1.5 times molar of alkali trithiocarbonate to N-(3-chloro-2-D-methylpropanoyl)-L-proline is required to reduce the formation of the monosulfide compound and the reaction temperature of about higher than 60° C. is effective to proceed with the reaction of N-(3-chloro-2-D-methylpropanoyl)-L-proline with alkali trithiocarbonate. This unexpected result, especially as for the extent of the formation of the monosulfide compound, in the reaction using the compound (II) can not be anticipated by a person of ordinary skill in the art from the results of the reaction using N-(3-bromo-2-D-methylpropanoyl)-L-proline. In the reaction using N-(3- bromo-2-D-methylpropanoyl)-L-proline the molar ratio of alkali trithiocarbonate is not important factor to reduce the formation of the monosulfide compound.

Thus it has been clarified by the present invention that the selection of the optimum and restricted reaction conditions (molar ratio of alkali trithiocarbonate to N-(3-chloro-2-D-methylpropanoyl)-L-amino acid and reaction temperature) is the important factor to produce N-(3-mercapto-2-D-methylpropanoyl)-L-amino acid using N-(3-chloro-2-D-methylpropanoyl)-L-amino acid as a starting material. Further it is an advantageous feature of the present invention that the reaction can be conducted in higher concentration of the starting material, with depressing the formation of the by-product, and the configuration of the optically active starting material in the process is retained. Thus the present invention has eliminated the foregoing drawback of known processes, thus providing an advantageous process for preparing the optically active N-(3-mercapto-2-D-methylpropanoyl)-L-amino acid from industrially available N-(3-chloro-2-D-methylpropanoyl)-L-amino acid.

DETAILED DESCRIPTION OF THE INVENTION

According to the process of the present invention, the optically active N-(3-mercapto-2-D-methylpropanoyl)-L-amino acid (I) can readily be obtained by the reaction of N-(3-chloro-2-D-methylpropanoyl)-L-amino acid (II) with an alkali trithiocarbonate of which the molar ratio to the compound (II) is not less than 1.5 in water at a temperature of from about 60° C. to about 90° C. followed by hydrolysis of the resulting product with an acid.

As the alkali trithiocarbonate is used, for example sodium trithiocarbonate, potassium trithiocarbonate or ammonium trithiocarbonate. Sodium trithiocarbonate is the most preferable among these. Sodium trithiocarbonate is readily prepared from sodium sulfide and carbon disulfide in water and the resulting aqueous solution can be used in the subsequent reaction, but the attention should be called to the residual sodium sulfide, which causes the formation of the by-product, monosulfide compound (III).

As described above in comparison with known methods for the conversion of chlorine into thiol group, the molar ratio of the alkali trithiocarbonate to the compound (II) is important to minimize the side reaction and to obtain pure N-(3-mercapto-2-D-methylpropanoyl)-L-amino acid in higher yield. The molar ratio of the alkali trithiocarbonate to the compound (II) is not less than 1.5, preferably from about 1.5 to 2.0. The use of alkali trithiocarbonate of which the molar ratio is less than 1.5 causes the appreciable amount of the by-product, monosulfide compound, and consequently causes the lowering of the yield and the purity of the compound (I). The use of the larger excess of the alkali trithiocarbonate does not result in further increasing the yield and the purity of the compound (I), and the molar ratio from about 1.5 to 2.0 is preferably employed.

The reaction of the compound (II) with alkali trithiocarbonate is conducted by the mixing of N-(3-mercapto-2-D-methylpropanoyl)-L-amino acid, its alkali metal salt or its ammonium salt and aqueous alkali trithiocarbonate. The reaction is carried out in water or in aqueous alcohol such as aqueous methanol or ethanol, but practically water is the most preferable. The concentration of the starting material, the compound (II), is not the important factor in the reaction yield, and can be selected from about 5 wt % to about 20 wt %. After the mixing of the reactants the temperature of the reaction mixture is raised. The reaction is carried out at a temperature of 50° C. to 100° C. over a period of from 10 to 3 hrs, preferably at a temperature from about 60° C. to about 90° C. over a period of from 7 to 4 hrs. At a temperature below 60° C., the yield of the product is low (30% for 4 hrs) and it takes longer time to complete the reaction. The reaction at a temperature above 90° C. is inadequate because the racemization and decomposition of the compounds occurs gradually under alkaline condition.

After the disappearance of the starting material, the compound (II), the reaction mixture is acidified to pH 1 ~ pH 2 with mineral acid such as hydrochloric acid or sulfuric acid. Subsequently, hydrogen sulfide and carbon disulfide evolved by acidification are removed by distillation, and then the desired product, N-(3-mercapto-2-D-methylpropanoyl)-L-amino acid, is extracted with organic solvent such as ethyl acetate, methylene chloride or chloroform.

The crude product of N-(3-mercapto-2-D-methylpropanoyl)-L-amino acid sometimes contains a small amount of the disulfide derivative of the compound (I) represented by formula (IV).

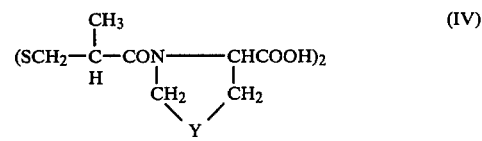

Y=CH$_2$ or S

This compound can easily be converted to the desired product, the compound (I), by subjecting the crude product to reduction with Zn/sulfuric acid, Zn/hydrochloric acid or Fe/sulfuric acid.

The reduction can be carried out by adding Zn or Fe powder to the acidic reaction mixture before extraction with organic solvent.

Thus the process of the present invention is very simplified and economical in order to produce the optically active N-(3-mercapto-2-D-methylpropanoyl)-L-amino acid starting from industrially available N-(3-chloro-2-D-methylpropanoyl)-L-amino acid.

To further illustrate the present invention, and not by way of limitation, the following examples are given.

EXAMPLE 1

Na$_2$S.9H$_2$O (33.0 g) was dissolved in 100 ml of H$_2$O and 11.6 g of CS$_2$ was added. The reaction mixture was warmed to 40° ~ 45° C. for 4 hrs with stirring in a reaction vessel equipped with reflux condenser. Excess CS$_2$ was removed by distillation and 128 ml of aqueous sodium trithiocarbonate was obtained. To 32 ml of this solution, 6 ml of an aqueous solution containing 4.18 g of N-(3-chloro-2-D-methylpropanoyl)-L-proline sodium salt was added and warned up to 85° C. for 5 hrs with stirring, then cooled to room temp. and acidified to pH 1 with 35% hydrochloric acid. The reaction mixture was kept for 1 hr with stirring, and extracted with ethyl acetate. After the evaporation of ethyl acetate 4.0 g of syrup was obtained. The composition of the syrup was measured with HPLC. N-(3-mercapto-2-D-methylpropanoyl)-L-proline: 3.3 g, monosulfide compound: 0.015 g, disulfide compound: 0.15 g;

This syrup was dissolved in 40 ml of 1 N-$H_2SO_4$ and to the solution 0.25 g of Zn powder was added. The mixture was stirred at room temp. for 2 hrs and extracted with ethyl acetate. After the evaporation of ethyl acetate 3.3 g of syrup was obtained.

3.0 g of N-(3-mercapto-2-D-methylpropanoyl)-L-proline was obtained as a white powder by adding n-hexane to ethyl acetate solution of the syrup. Yield: 79.8 mole %. m.p. 105° ~ 106° C., $[\alpha]_D^{25} = -129.0°$ (c:1, 99% EtOH).

Assay measurement of the product by HPLC was as follows:

N-(3-mercapto-2-D-methylpropanoyl)-L-proline: 99.0 wt %
monosulfide compound: 0.3 wt %
disulfide compound: 0.6 wt %

Comparative Experiment

To 32 ml of aqueous sodium trithiocarbonate prepared according to Example 1, 6.8 g of N-(3-chloro-2-D-methylpropanoyl)-L-proline was added, and thereafter the temperature was elevated to 40° C.

the reaction mixture was kept for 4 hrs with stirring, acidified after the reaction and extracted in the same way as in ex. 1. 5.8 g of syrup was obtained by concentrating the organic layer.

The syrup was subjected to analysis with HPLC, and found to contain 2.0 g of N-(3-mercapto-2-D-methylpropanoyl)-L-proline, and 4.1 g of a starting material. Yield was 30%.

EXAMPLE 2

Using 32 ml of aqueous sodium trithiocarbonate prepared in the same manner as described in Example 1, the reactions of N-(3-chloro-2-D-methylpropanoyl)-L-proline sodium salt with sodium trithiocarbonate were investigated under several conditions.

After the reaction the reaction mixture was acidified in the same manner as described in Example 1, and the acidic solution was subjected to the reduction with Zn powder. The products were extracted with ethyl acetate and analyzed by HPLC.

TABLE 1

| | Concentration of CBP (wt %) | Molar ratio Na$_2$CS$_3$/ CBP | React. temp React. time | | Yield of CTP (mole %) | Content* of Monosulfide (wt %) |
|---|---|---|---|---|---|---|
| 1 | 5.2 | 2.0 | 85° C. | 5.0 Hr | 84 | 0.3 |
| 2 | 7.0 | 1.2 | 75° C. | 100 Hr | 74 | 6.5 |
| 3 | 9.0 | 1.2 | 85° C. | 5.0 Hr | 71 | 6.7 |
| 4 | 9.0 | 1.5 | 85° C. | 5.0 Hr | 85 | 0.5 |
| 5 | 9.0 | 2.0 | 60° C. | 7.0 Hr | 79 | 0.3 |
| 6 | 10.5 | 2.0 | 85° C. | 5.0 Hr | 88 | 0.4 |
| 7 | 14.8 | 1.3 | 85° C. | 5.0 Hr | 77 | 2.0 |

*Wt % of monsulfide compound in the product obtained by extraction.
CBP: N—(3-chloro-2-D-methylpropanoyl)-L-proline
CTP: N—(3-mercapto-2-D-methylpropanoyl)-L-proline

EXAMPLE 3

To 32 ml of aqueous sodium trithiocarbonate prepared in the same manner as described in Example 1, 3.8 g of N-(3-chloro-2-D-methylpropanoyl)-L-proline was added and the mixture was stirred at 85° C. for 5 hrs. After the reaction the mixture was cooled to room temp., acidified to pH 1 with 50% sulfuric acid, then extracted with methylene chloride. After the evaporation of methylene chloride 4.0 g of syrup was obtained. The syrup was dissolved in 40 ml of 1 N-sulfuric acid and stirred for 3 hrs adding 0.5 g of Zn powder. After the reduction, the reaction mixture was extracted with methylene chloride, the organic layer was concentrated, 3.2 g of syrup was obtained. (Yield: 85.1 mol %).

This syrup, which changed to a white solid by standing, was found by analysis with HPLC to contain 99.1 wt % of N-(3-mercapto-2-D-methylpropanoyl)-L-proline and 0.4 wt % of monosulfide compound. $[\alpha]_D^{25} = -128.5°$ (c:1, 99% EtOH) m.p. 105° ~ 106° C.

EXAMPLE 4

To 32 ml of aqueous solution of sodium trithiocarbonate prepared in the same manner as described in Example 1, aqueous solution containing 4.5 g of N-(3-chloro-2-D-methylpropanoyl)-L-thiazolidine-4-carboxylic acid sodium salt (10 ml) was added and stirred at 80° C. for 6 hrs. The reaction mixture was cooled to room temp., acidified to pH 1 with 50% sulfuric acid, and then stirred for 2 hrs. To the acidic mixture 0.6 g of Zn powder was added and stirred at room temp. for 4 hrs.

The reaction mixture was extracted with ethyl acetate, the ethyl acetate of the extract was distilled off, and 3.9 g of syrup was obtained. 3.3 g of N-(3-mercapto-2-D-methylpropanoyl)-L-thiazolidine-4-carboxylic acid was obtained as a white power by precipitation from n-hexane/ethyl acetate. Yield: 82.5 mole %, $[\alpha]_D^{25} = -172.0°$ C. (c:1, MeOH) m.p. 92° ~ 94° C.

EXAMPLE 5

The reactions of N-(3-halo-2-D-methylpropanoyl)-L-proline with sodium trithiocarbonate under various conditions were investigated in a similar manner as described above. The reaction mixture was acidified with 50% sulfric acid, extracted with ethyl acetate, and the organic layer was concentrated to dryness. The residue was subjected to analysis with HPLC to clarify the difference in the reactivity between N-(3-chloro-2-D-methylpropanoyl)-L-proline and N-(3-bromo-2-D-methylpropanoyl)-L-proline.

TABLE 2

| | Substrate# | Concentration of substrate# | Molar ratio Na$_2$CS$_3$/ Substrate# | React. temp React. time | | Yield (CTP) (mole %) | Content of* Monosulfide |
|---|---|---|---|---|---|---|---|
| 1 | CBP | 17.5 wt % | 1.2 | 40° C. | 4 Hr | 29% | |
| 2 | CBP | 7.7 wt % | 1.2 | 85° C. | 3 Hr | 73% | 10.0% |
| 3 | CBP | 9.0 wt % | 1.2 | 85° C. | 5 Hr | 71% | 6.7% |
| 4 | CBP | 9.0 wt % | 2.0 | 60° C. | 7 Hr | 79% | 0.3% |
| 5 | CBP | 9.0 wt % | 1.5 | 85° C. | 5 Hr | 85% | 0.5% |
| 6 | BBP | 8.5 wt % | 1.2 | 40° C. | 3 Hr | 76% | 1.0% |
| 7 | BBP | 8.5 wt % | 1.2 | 85° C. | 3 Hr | 84% | 1.5% |
| 8 | BBP | 8.5 wt % | 1.5 | 40° C. | 3 Hr | 87% | 0.2% |

TABLE 2-continued

| Sub-strate# | Concentration of substrate# | Molar ratio Na2CS3/Substrate# | React. temp React. time | | Yield (CTP) (mole %) | Content of* Monosulfide |
|---|---|---|---|---|---|---|
| 9 BBP | 8.5 wt % | 1.5 | 85° C. | 3 Hr | 90% | 0.6% |

CTP: N—(3-mercapto-2-D-methylpropanoyl)-L-proline
CBP: N—(3-chloro-2-D-methylpropanoyl)-L-proline
BBP: N—(3-bromo-2-D-methylpropanoyl)-L-proline
*Wt % of monosulfide compound in the product obtained by extraction.
"substrate" means "starting material"

What is claimed is:

1. A process for preparation of an optically active N-(3-mercapto-2-D-methylpropanoyl)-L-amino acid represented by formula (I):

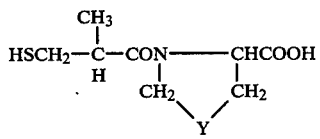

wherein Y is CH₂ or sulfur which comprises
(1) reacting an N-(3-chloro-2-D-methylpropanoyl)-L-amino acid represented by formula (II):

$$\text{ClCH}_2-\underset{\underset{H}{|}}{\overset{\overset{CH_3}{|}}{C}}-CON\underset{\underset{Y}{\diagdown\diagup}}{\overset{\diagup\phantom{Y}\diagdown}{\underset{CH_2\phantom{Y}CH_2}{|\phantom{YY}|}}}CHCOOQ \qquad (II)$$

wherein Y is the same as defined above, and Q is hydrogen, Na, K, or NH₄,
with an alkali trithiocarbonate of which the molar ratio to the compound (II) is not less than 1.5 in water at a temperature of from about 60° C. to about 90° C.; and
(2) hydrolyzing the resulting product with an acid.

2. The process according to claim 1 wherein the alkali trithiocarbonate is sodium trithiocarbonate.

3. The process according to claim 1 wherein the acid is a mineral acid.

4. The process according to claim 2 wherein the acid is a mineral acid.

5. The process according to claim 1, wherein Y is sulfur.

* * * * *